(12) United States Patent
Yoshikawa et al.

(10) Patent No.: US 8,673,976 B2
(45) Date of Patent: Mar. 18, 2014

(54) MEDICAMENT FOR PROPHYLACTIC AND/OR THERAPEUTIC TREATMENT OF HEPATIC STEATOSIS OR NON-ALCOHOLIC STEATOHEPATITIS

(75) Inventors: Yuji Yoshikawa, Tokyo (JP); Megumi Yamamoto, Kyoto (JP); Naoto Ishibashi, Saitama (JP); Mami Seki, Saitama (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 13/524,134

(22) Filed: Jun. 15, 2012

(65) Prior Publication Data

US 2012/0259015 A1  Oct. 11, 2012

Related U.S. Application Data

(62) Division of application No. 12/593,053, filed as application No. PCT/JP2008/000760 on Mar. 27, 2008, now abandoned.

(30) Foreign Application Priority Data

Mar. 30, 2007  (JP) ................................. 2007-090114

(51) Int. Cl.
*A01N 37/00* (2006.01)
(52) U.S. Cl.
USPC ........................................................ 514/560
(58) Field of Classification Search
USPC ........................................................ 514/560
See application file for complete search history.

(56) References Cited

U.S. PATENT DOCUMENTS

| | | | |
|---|---|---|---|
| 4,655,973 | A | 4/1987 | Yamatsu et al. |
| 4,917,829 | A | 4/1990 | Yamatsu et al. |
| 4,988,732 | A | 1/1991 | Yamatsu et al. |
| 5,922,345 | A | 7/1999 | Horrobin et al. |
| 2005/0250671 | A1 | 11/2005 | Shidoji et al. |
| 2006/0094784 | A1 | 5/2006 | Kagawa et al. |
| 2008/0021105 | A1 | 1/2008 | Nagai et al. |
| 2008/0146664 | A1 | 6/2008 | Okuyama et al. |

FOREIGN PATENT DOCUMENTS

| | | |
|---|---|---|
| JP | 04-290821 | 10/1992 |
| JP | 09-194362 | 7/1997 |
| JP | 2002-104965 | 4/2002 |
| JP | 2006-232711 | 9/2006 |
| JP | 2007-314492 | 12/2007 |
| JP | 2008-150307 | 7/2008 |
| WO | 01/80854 | 11/2001 |
| WO | 03/097034 | 11/2003 |
| WO | 2005/079783 | 9/2005 |

OTHER PUBLICATIONS

Harano et al, Liver International, 2006, 26, 613-620.*
Tanaka et al., "Role of PPARs in the Pathophysiology of Nonalcoholic Fatty Liver Disease", *Japanese Journal of Clinical Medicine*, vol. 63, No. 4, pp. 700-706, 2005.
Factor et al., "Disruption of Redox Homeostasis in the Transforming Growth Factor-α/c-*myc* Transgenic Mouse Model of Accelerated Hepatocarcinogenesis" *J. Biol. Chem.*, vol. 273, No. 25, pp. 15846-15853, 1998.
Takeda et al., "KLF5 Inhibitor Am80 Reduces Atherosclerosis, Adipose Tissue Growth, and Fatty Liver Disease" *Circulation*, vol. 110, No. 17, p. 786, 2004.
Muto et al., "Prevention of of Second Primary Tumors by an Acyclic Retinoid, Polyprenoic Acid, in Patients with Hepatocellular Carcinoma" Hepatoma Prevention Study Group, *N. Engl. J. Med.*, vol. 334, No. 24, pp. 1561-1567, 1996.
International Search Report issued in connection with PCT/JP2008/000760 May 13, 2008.
International Preliminary Report on Patentability issued in connection with PCT/JP2008/000760 Oct. 13, 2009.
David Langsam: "Solagran Hails Australian Ropren Trial" [Online] Biotech Daily, New Bites Pty Ltd, p. 2PP, Feb. 22, 2007; Retrieved from the internet: URL: http://www.swinburne.edu.au/corporate/marketing/mediacentre/core/content/print_articles_070219_part2.pdf, XP002607263.
Database Accession No. 679490, Database Integrity [Online] Thomson Reuters, "Bioeffective R/Ropren" Oct. 27, 2010; XP002607265.
Keischs J. et al. "The Treatment of Primary Biliary Cirrhosis with Ropren" Database Biosis [Online], Database Accession No. PREV199799629757, 1997; XP009140620.
Extended European Search Report for EP App. No. 08720639.7, dated Nov. 30, 2010.
European Office Action issued with respect to counterpart European Application No. 08 720 639.7, dated May 30, 2012.
Schuller et al., "Russia recommends approval of Solagran liver disease drug", Life Scientist, http://www.lifescientist.com.au/article/149043/, Jan. 27, 2006, pp. 1-3.
Bershad et al., N. Engl. J. Med., 313, 981-985 (1985).
NCBI Pubchem—Accutance (TN)—Pubchem downloaded from http://pubchem.ncbi.nlm.nih.gov/summary/summary.cgi?sid=7847414.
Japanese Office Action for Japanese Appl. No. 2009-508889, mailed Dec. 18, 2012.
Japanese Notice of Rejection for Japanese Appl. No. 2009-508889, mailed Mar. 26, 2013.

* cited by examiner

*Primary Examiner* — Jason M Sims
*Assistant Examiner* — Ibrahim D Bori
(74) *Attorney, Agent, or Firm* — Greenblum & Bernstein, P.L.C.

(57) ABSTRACT

A medicament for prophylactic and/or therapeutic treatment of hepatic steatosis or non-alcoholic steatohepatitis, which comprises a polyprenyl compound (e.g., 3,7,11,15-tetramethyl-2,4,6,10,14-hexadecapentaenoic acid) as an active ingredient.

9 Claims, 3 Drawing Sheets

*P<0.05 vs. normal control group
MEAN±S.E. (n=8)

*P<0.05 vs. normal control group
MEAN±S.E. (n=8)

*P<0.05 vs. control group
MEAN±S.E. (n=4-5)

*P<0.05 vs. control group
MEAN±S.E. (n=5)

MEDICAMENT FOR PROPHYLACTIC AND/OR THERAPEUTIC TREATMENT OF HEPATIC STEATOSIS OR NON-ALCOHOLIC STEATOHEPATITIS

RELATED APPLICATIONS

The present application is a Divisional of U.S. application Ser. No. 12/593,053, which is a national stage of International Application No. PCT/JP2008/000760, filed Mar. 27, 2008, which claims priority to Japanese Patent Application No. 2007-090114, filed Mar. 30, 2007. The disclosures of Application No. 12/593,053 and PCT/JP2008/000760 are expressly incorporated by reference herein in their entireties.

TECHNICAL FIELD

The present invention relates to a medicament for prophylactic and/or therapeutic treatment of hepatic steatosis or non-alcoholic steatohepatitis. More specifically, the present invention relates to a medicament for prophylactic and/or therapeutic treatment of hepatic steatosis or non-alcoholic steatohepatitis, which comprises a polyprenyl compound as an active ingredient, preferably a medicament comprising (2E,4E,6E,10E)-3,7,11,15-tetramethyl-2,4,6,10,14-hexadecapentaenoic acid.

BACKGROUND ART

In recent years, consumption of fats has been increasing every year in Japan with westernization of lifestyles including eating habits. It is known that fats excessively taken up are gradually accumulated in bodies, and become factors of inducing various diseases. Mechanisms of the fat accumulation is roughly classified into the following two classes. According to one of the mechanisms, excessive fats existing in blood deposit on blood vessel walls, which leads to stenosis of blood vessels to gradually develops into arteriosclerosis, and some time later triggers the onset of myocardial infarction, angina pectoris, cerebral infarction, and the like. According to the other mechanism, excessive fats similarly deposit in visceral organs. In particular, so-called hepatic steatosis, in which a lot of fats deposit in the liver, has recently been frequently observed, and some of hepatic steatosis advance at some future to non-alcoholic steatohepatitis, cirrhosis, and hepatoma (Gastroenterology, 116, 1413-1419 (1999)). The aforementioned diseases are based on the different onset mechanisms, and accordingly, a medicament suitable for prophylactic and/or therapeutic treatment of each disease is needed.

As a therapeutic agent of hepatic steatosis, polyenephosphatidylcholine has been clinically used. Further, fibrate agents, of which typical examples include clofibrate as an antihyperlipidemic agent, have also been clinically used as therapeutic agents for hepatic steatosis. It is considered that the fibrate agents improve lipid metabolism by acting on enzymes for fatty acid β-oxidation system in the liver (Ann. N.Y. Acad. Sci., 386, 111-135 (1982)). However, side reactions such as liver function failure are generally known for the fibrate agents (Atherosclerosis, 92, 31-40 (1992)), and therefore a medicament for prophylactic and/or therapeutic treatment of hepatic steatosis or non-alcoholic steatohepatitis with less side effects has been desired.

(2E,4E,6E,10E)-3,7,11,15-Tetramethyl-2,4,6,10,14-hexadecapentaenoic acid, which is one of polyprenyl compounds and has a chemical structure totally different from those of polyenephosphatidylcholine and the fibrate agents mentioned above, is a acyclic retinoid having affinity for retinoic acid binding proteins and retinoic acid receptors, and actions thereof for inducing differentiation and inducing apoptosis in hepatocellular carcinoma are known. Clinically, (2E,4E,6E,10E)-3,7,11,15-tetramethyl-2,4,6,10,14-hexadecapentaenoic acid significantly inhibited recurrence of hepatoma after radical treatment thereof by long-term administration for one year, and thus suppressing action thereof on the recurrence of hepatoma was suggested. Further, liver function failure or other adverse effects, those caused by retinoids, were not substantially observed during the administration thereof, and therefore the compound was revealed to be a safe medicament (N. Eng. J. Med., 334, 1561-1567 (1996)).

However, it was not known that polyprenyl compounds had prophylactic and therapeutic effectiveness on hepatic steatosis or non-alcoholic steatohepatitis.

Non-patent document 1: Gastroenterology, 116, pp. 1413-1419 (1999)
Non-patent document 2:Ann. N.Y. Acad. Sci., 386, pp. 111-135 (1982)
Non-patent document 3:Atherosclerosis, 92, pp. 31-40 (1992)
Non-patent document 4: N. Eng. J. Med., 334, pp. 1561-1567 (1996)

DISCLOSURE OF THE INVENTION

Object to be Achieved by the Invention

An object of the present invention is to provide a medicament for prophylactic and/or therapeutic treatment of hepatic steatosis or non-alcoholic steatohepatitis.

More specifically, the object of the present invention is to provide a medicament for prophylactic and/or therapeutic treatment of hepatic steatosis or non-alcoholic steatohepatitis with reduced side effects.

Means for Achieving the Object

The inventors of the present invention conducted various researches to find a medicament for prophylactic and/or therapeutic treatment of hepatic steatosis or non-alcoholic steatohepatitis. As a result, it was found that polyprenyl compounds reduced an amount of lipids in the liver. The present invention was accomplished on the basis of the above finding.

The present invention thus relates to the followings.

[1] A medicament for prophylactic and/or therapeutic treatment of hepatic steatosis or non-alcoholic steatohepatitis, which comprises a polyprenyl compound as an active ingredient.
[2] The medicament according to [1], wherein the polyprenyl compound is a polyprenylcarboxylic acid.
[3] The medicament according to [1], wherein the polyprenyl compound is 3,7,11,15-tetramethyl-2,4,6,10,14-hexadecapentaenoic acid.
[4] The medicament according to [1], wherein the polyprenyl compound is (2E,4E,6E,10E)-3,7,11,15-tetramethyl-2,4,6,10,14-hexadecapentaenoic acid.
[5] The medicament according to any one of [1] to [4], which is in the form of a pharmaceutical composition containing a pharmacologically acceptable pharmaceutical carrier.
[6] The medicament according to any one of [1] to [5], which is a preparation for oral administration.
[7] Use of a polyprenyl compound for manufacture of the aforementioned medicament.
[8] A method for prophylactic and/or therapeutic treatment of hepatic steatosis or non-alcoholic steatohepatitis, which comprises the step of administrating a prophylactically and/or therapeutically effective amount of a polyprenyl compound to a mammal including human.

BEST MODE FOR CARRYING OUT THE INVENTION

Figure 1:
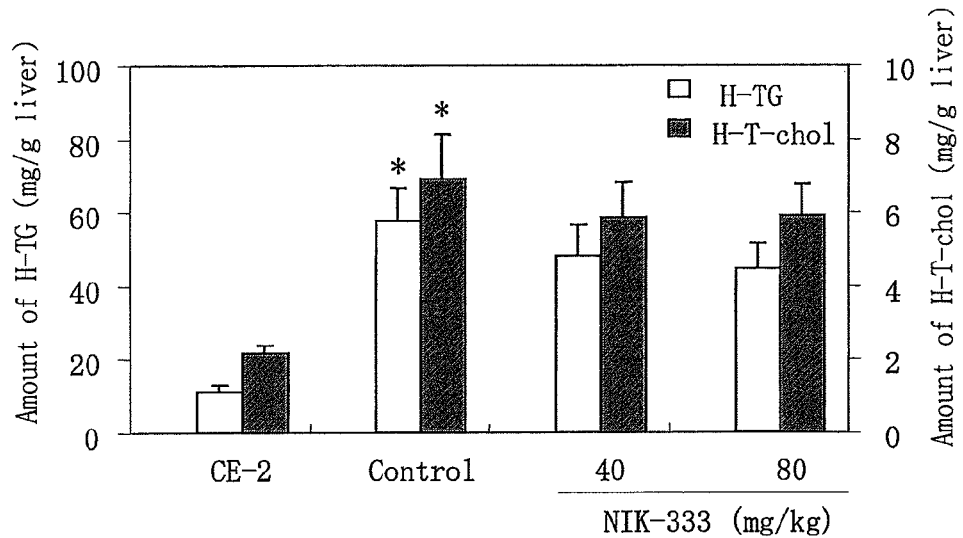
FIG. 1 is a graph showing the amounts of H-TG (mg/g liver) and the amounts of H-T-chol (mg/g liver) observed for the groups in Example 1. In the graph, the symbol * means a significant difference (P<0.05) compared with the normal control group.

The polyprenyl compounds used for the medicament of the present invention mean compounds having several linear isoprene units in the chemical structure. Preferred compounds include polyprenylcarboxylic acids having carboxy group at the end, and a particularly preferred compound includes (2E,4E,6E,10E)-3,7,11,15-tetramethyl-2,4,6,10,14-hexadecapentaenoic acid (henceforth referred to as NIK-333). Other examples of the polyprenyl compounds include conjugated polyprenylcarboxylic acids (polyprenoic acids) such as 3,7,11,15-tetramethyl-2,4,6,10,14-hexadecapentaenoic acid and esters thereof described in Japanese Patent Publication (Kokoku) No. 63-34855, and the like.

The polyprenyl compounds used in the present invention can be synthesized by a known method (Japanese Patent Publication No. 63-32058; J. Chem. Soc. (C), 2154 (1966)).

When the polyprenyl compounds are used for the medicament for prophylactic and/or therapeutic treatment of hepatic steatosis or non-alcoholic steatohepatitis of the present invention, said compounds can be administered by an appropriate administration method such as oral administration or parenteral administration. Examples of forms for oral administration include, for example, tablets, granules, capsules, soft capsules, pills, powders, solutions, and the like. Examples of forms for parenteral administration include, for example, injections, suppositories, and the like. These preparations can be prepared by a conventional method using a polyprenyl compound or a pharmacologically acceptable salt thereof and one or more kinds of ordinary pharmaceutical carriers.

For example, in the case of preparation for oral administration, desired administration forms can be prepared by using excipients such as lactose, glucose, corn starch and sucrose, disintegrating agents such as carboxymethylcellulose calcium and hydroxypropylcellulose, lubricants such as calcium stearate, magnesium stearate, talc, polyethylene glycol and hydrogenated oil, binders such as hydroxypropylcellulose, hydroxypropylmethylcellulose, carboxymethylcellulose, polyvinyl alcohol, gelatin and gum arabic, and moistening agents such as glycerin and ethylene glycol, as well as surfactants, flavoring agents and the like as required.

Further, in the case of preparation for parenteral administration, diluents such as water, ethanol, glycerin, propylene glycol, polyethylene glycol, vegetable oil, agar and tragacanth gum as well as dissolving aids, suspending agents, emulsifiers, stabilizers, buffers, isotonic agents, preservatives, soothing agents and the like can be used as required.

When the compounds are prescribed as the medicament for prophylactic and/or therapeutic treatment of hepatic steatosis or non-alcoholic steatohepatitis of the present invention, a dose may be 1 to 2,000 mg, preferably 20 and 800 mg, in terms of the compounds used for the present invention, per day for an adult in the case of oral administration. In the case of parenteral administration, the compounds are administered at a dose in the range of 1 to 1,000 mg, preferably in the range of 10 to 100 mg. Desired therapeutic effects can be expected by administering the compounds 1 to 3 times per day as divided portions of the aforementioned doses.

EXAMPLES

The present invention will be explained more specifically with reference to the following examples. However, the scope of the present invention is not limited to these examples.

Example 1

Evaluation of Action of NIK-333 for Decreasing Hepatic Lipid Amount

Figure 2:
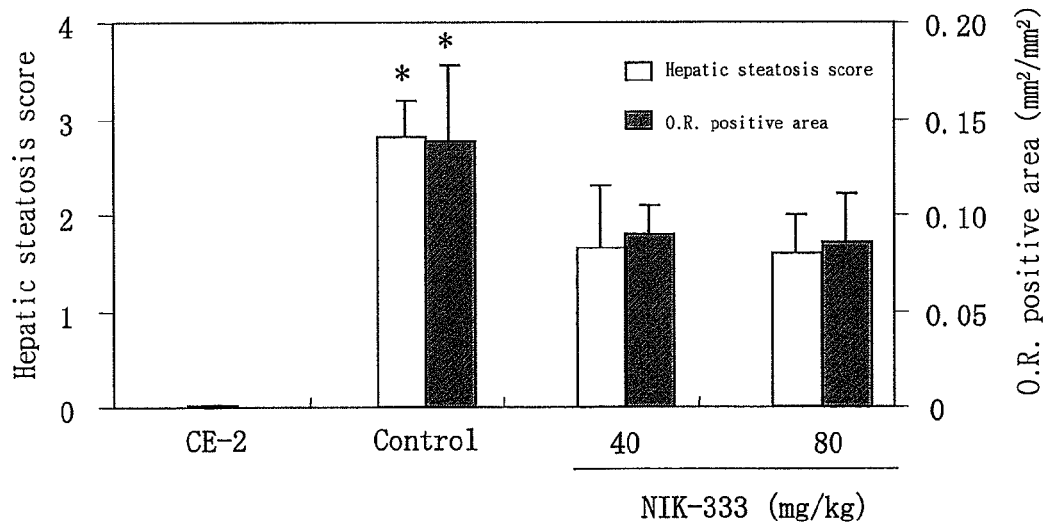
FIG. 2 is a graph showing the hepatic steatosis scores and the O.R. positive areas ($mm^2/mm^2$) observed for the groups in Example 1. In the graph, the symbol * means a significant difference (P<0.05) compared with the normal control group.
Figure 3:
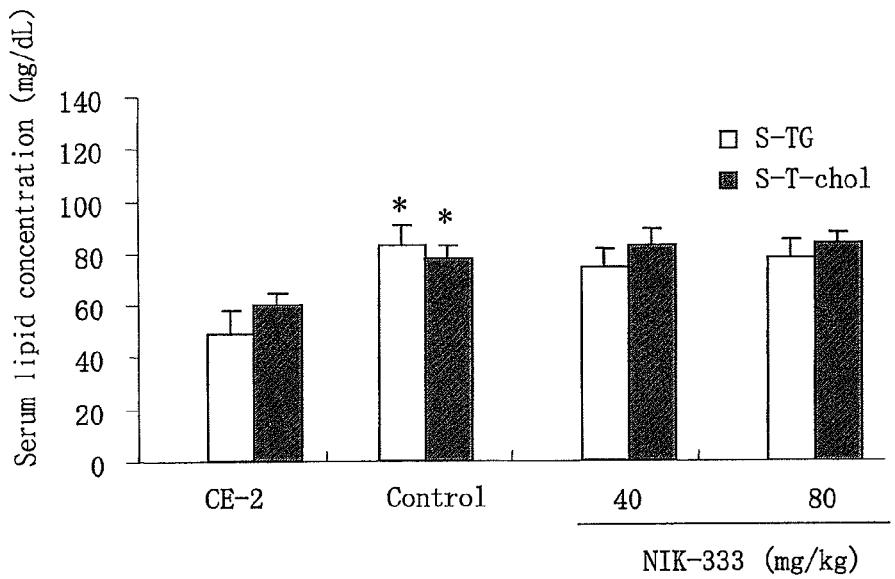
FIG. 3 is a graph showing the S-TG concentrations (mg/dL) and S-T-chol concentrations (mg/dL) observed for the groups in Example 1. In the graph, the symbol * means a significant difference (P<0.05) compared with the normal control group.
Figure 4:
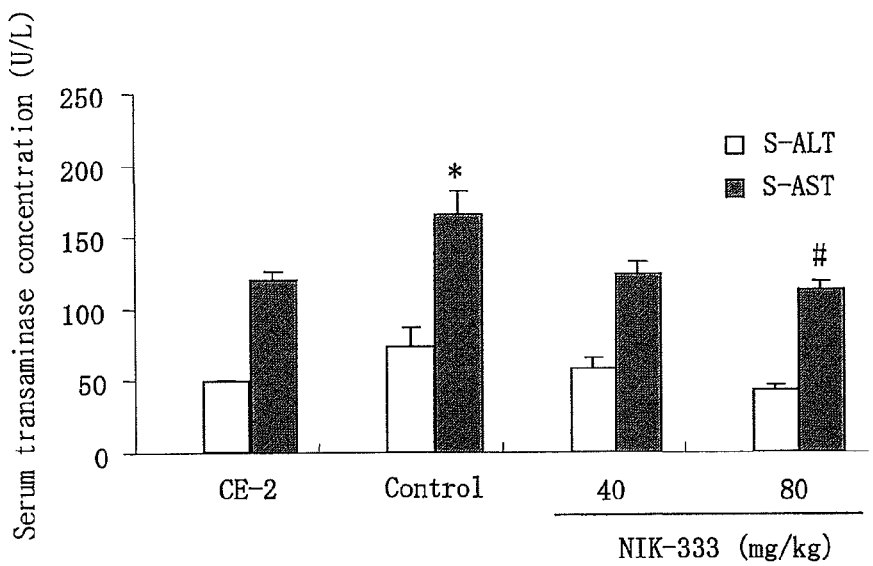
FIG. 4 is a graph showing the S-ALT concentrations (U/L) and the S-AST concentrations (U/L) observed for the groups in Example 1. In the graph, the symbols * and # mean a significant difference (P<0.05) compared with the normal control group and the control group, respectively.

For the experiment, 6-week old SD male rats (Charles River Japan) were used. HFD32 (Clea Japan) was used for the high fat diet group, and CE-2 (Clea Japan) was used for the normal control group. The feeding was restricted to 25±3 g for both of the groups. The feed ingredients are shown in Table 1. Administration of NIK-333 was started at the same time as the start of the loading of the high fat diet, and the drug was given once a day for 8 weeks by forcible continuous oral administration. After completion of the test, each liver was extracted, and triglyceride (H-TG) amount and cholesterol (H-T-chol) amount in the liver were measured. The results are shown in FIG. 1. Hematoxylin-eosin (H.E.) and Oil Red O (O.R.) staining samples were prepared from the extracted liver, and histopathological examination was performed. Degree of fatty degeneration of the liver was graded into five categories on the basis of the examination of the H.E. staining sample, and scores were assigned. Further, from the O.R. staining sample, O.R. positive area in the liver sample area was calculated by using an image analyzer. The results are shown in FIG. 2. Furthermore, triglyceride (S-TG), total cholesterol (S-T-chol), alanine aminotransferase (S-ALT), and aspartate aminotransferase (S-AST) levels in serum were measured. The results are shown in FIGS. 3 and 4.

TABLE 1

| Contents in 100 g of feed | | |
|---|---|---|
| Common ingredients | CE-2 | HFD32 |
| Moisture (g) | 9.2 | 6.9 |
| Crude protein (g) | 25.8 | 25.0 |
| Crude fat (g) | 4.0 | 32.4 |
| Crude fiber (g) | 3.8 | 2.9 |
| Crude ash (g) | 6.9 | 4.0 |
| Soluble non-nitrogen substance (g) | 50.5 | 28.8 |
| Energy (kcal) | 340.4 | 506.8 |

As shown in FIGS. 1 and 2, NIK-333 decreased the amount of lipids in the liver, and therefore, it was revealed that the compound has effectiveness on prophylactic and/or therapeutic treatment of hepatic steatosis or non-alcoholic steatohepatitis. It can be also understood that NIK-333 decreases the amount of lipids in the liver without affecting lipid concentration in blood as shown in FIG. 3. Generally, retinoids are pointed out to have a problem of inducing hypertriglyceridemia as a side effect in clinical use (N. Engl. J. Med., 313, 981-985 (1985)). However, NIK-333 does not show such increase in lipid concentration in blood. It can be recognized that NIK-333 has an suppressing effect on the increase of blood transaminase as shown in FIG. 4, and has an action of protecting the liver. From the above, it is clearly understood that NIK-333 has effectiveness on prophylactic and/or therapeutic treatment of hepatic steatosis or non-alcoholic steatohepatitis.

Example 2

Evaluation of NIK-333 and ATRA for Toxicity

Figure 5:
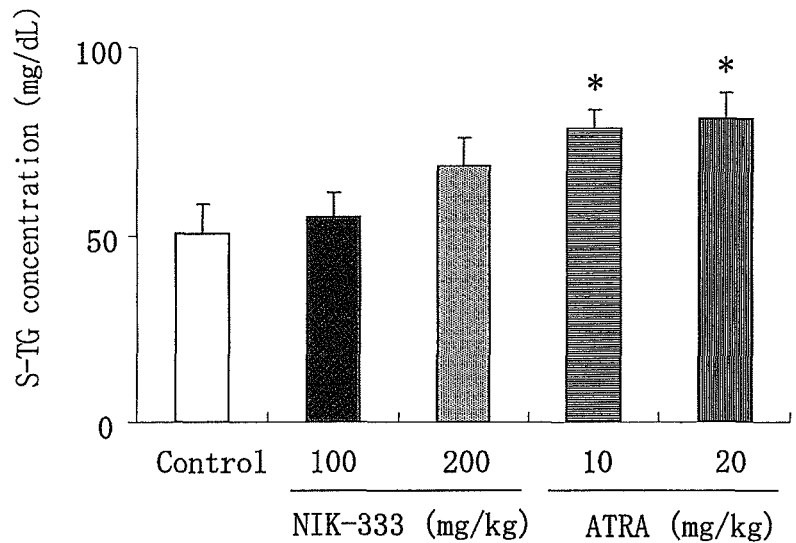
FIG. 5 is a graph showing the S-TG concentrations (mg/dL) observed for the groups in Example 2. In the graph, the symbol * means that a significant difference (P<0.05) compared with the control group.
Figure 6:
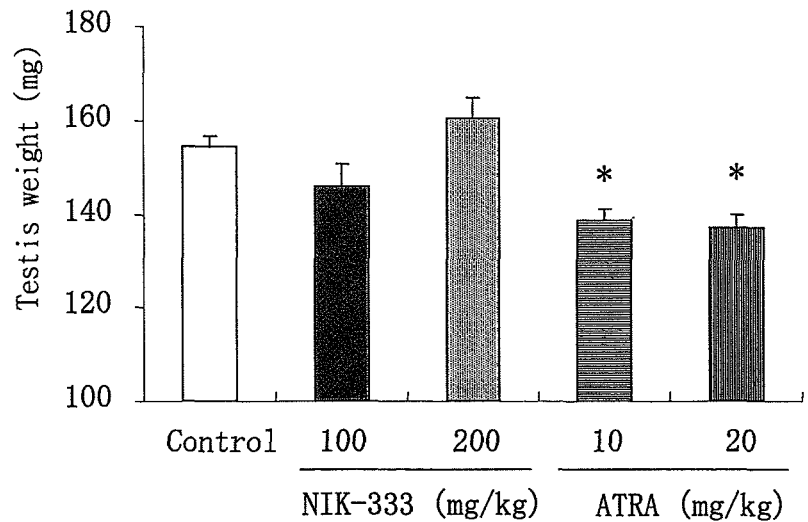
FIG. 6 is a graph showing the testis weights (mg) observed for the groups in Example 2. In the graph, the symbol * means a significant difference (P<0.05) compared with the control group.

7-Week old C57BL/6N mice (Charles River Japan) were given with MK-333 or ATRA once per day for 2 weeks by forcible continuous oral administration. After completion of the test, S-TG concentrations and testis weights of individual mice were measured. The results are shown in FIGS. 5 and 6, respectively. To the control group, soybean oil was administered.

As shown in FIG. 5, it can be understood that ATRA increases the S-TG concentration, whilst NIK-333 does not affect the concentration. It can be also recognized that ATRA markedly decreases testis weight, whilst NIK-333 does not affect the weight as shown in FIG. 6. It was observed that ATRA decreased testis weight in mice (Fundam. Appl. Toxicol., 8, 517-530 (1987)) and rats (Toxicology, 30, 115-124 (1984)), whilst the aforementioned action is not observed for NIK-333. From the above results, it is clearly understood that toxicity of NIK-333 for S-TG and testis is lower than that of ATRA.

From the above results, it can be concluded that the medicament of the present invention is useful as a novel medicament for use in prophylactic and/or therapeutic treatment of hepatic steatosis or non-alcoholic steatohepatitis.

Industrial Applicability

The medicament for prophylactic and/or therapeutic treatment of hepatic steatosis or non-alcoholic steatohepatitis provided by the present invention has an action of decreasing lipid amount in the liver and improving liver functions. The medicament has less effect on triglyceride (S-TG) concentration in blood serum and testis weight as compared with all-trans-retinoic acid (henceforth abbreviated as ATRA) as a cyclic retinoid, and thus a medicament with reduced side effects.

What is claimed is:

1. A method for prophylactic and/or therapeutic treatment of hepatic steatosis or non-alcoholic steatohepatitis in a mammal in need thereof, comprising administering to the mammal a composition comprising 3,7,11,15-tetramethyl -2,4,6,10,14-hexadecapentaenoic acid in an amount effective so that the 3,7,11,15-tetramethyl-2,4,6,10,14-hexadecapentaenoic acid decreases the amount of lipid in the liver and does not increase the amount of lipid in the blood.

2. The method according claim 1, wherein the prophylactic and/or therapeutic treatment is therapeutic treatment of hepatic steatosis or non-alcoholic steatohepatitis.

3. The method according to claim 2, wherein the 3,7,11,15-tetramethyl-2,4,6,10,14-hexadecapentaenoic acid is (2E,4E,6E,10E)-3,7,11,15-tetramethyl-2,4,6,10,14-hexadecapentaenoic acid.

4. The method according to claim 2, wherein the composition contains a pharmacologically acceptable pharmaceutical carrier.

5. The method according to claim 2, wherein the composition is a preparation for oral administration.

6. The method according to claim 2, wherein the mammal is a human.

7. The method according to claim 3, wherein the composition contains a pharmacologically acceptable pharmaceutical carrier.

8. The method according to claim 3, wherein the composition is a preparation for oral administration.

9. The method according to claim 3, wherein the mammal is a human.

* * * * *